(12) United States Patent
Pellicciari et al.

(10) Patent No.: US 6,989,388 B2
(45) Date of Patent: Jan. 24, 2006

(54) THIENO[2,3-C]IOSQUINOLINES FOR USE AS INHIBITORS OF PARP

(75) Inventors: Roberto Pellicciari, GlaxoSmithKline Corporate Intellectual Property-UW2220 P.O. Box 1539, King of Prussia, PA (US) 19406-0939; Flavio Moroni, GlaxoSmithKline Corporate Intellectual property-UW2220 P.O. Box 1539, King of Prussia, PA (US) 19406-0939

(73) Assignees: Roberto Pellicciari, Perugia (IT); Flavio Moroni, Florence (IT)

( * ) Notice: Subject to any disclaimer, the term of this patent is extended or adjusted under 35 U.S.C. 154(b) by 0 days.

(21) Appl. No.: 10/415,601

(22) PCT Filed: Oct. 30, 2001

(86) PCT No.: PCT/IB01/02030

§ 371 (c)(1),
(2), (4) Date: Dec. 18, 2003

(87) PCT Pub. No.: WO02/36599

PCT Pub. Date: May 10, 2002

(65) Prior Publication Data

US 2004/0082789 A1    Apr. 29, 2004

(30) Foreign Application Priority Data

Oct. 31, 2000    (IT) .............................. MI00A2358

(51) Int. Cl.
*A61K 31/4743* (2006.01)
*C07D 495/06* (2006.01)

(52) U.S. Cl. .......................... 514/291; 546/80; 546/84; 546/89; 546/70; 546/62; 514/285; 514/292

(58) Field of Classification Search ................ 514/291, 514/292, 285; 546/80, 84, 89, 70, 62
See application file for complete search history.

(56) References Cited

U.S. PATENT DOCUMENTS

| 4,113,731 A | 9/1978 | Winters et al. |
| 4,263,304 A | * 4/1981 | Ishizumi et al. ............ 414/262 |

FOREIGN PATENT DOCUMENTS

| WO | WO 99/11645 | 11/1999 |
| WO | WO 99/59975 | 11/1999 |

OTHER PUBLICATIONS

Compound having RN 74796-97-7.*
S. Kano et al., "A facile synthesis of 4-phenylcarbostyrils and 4-phenylisocarbostyril involving photocyclization of . . . ", (1979), Heterocycles, 12(4), pp. 489-492.

* cited by examiner

*Primary Examiner*—Charanjit S. Aulakh
(74) *Attorney, Agent, or Firm*—Michael P. Straher; Cozen O'Connor

(57) ABSTRACT

The present invention relates to compounds for the inhibition of poly(ADP-ribose) polymerase (PARP). In some embodiments, the compounds have the Formula:

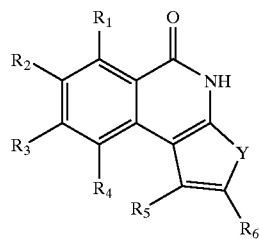

wherein the constituent variables are as defined herein. The invention further provides methods for the use of the compounds disclosed herein.

17 Claims, No Drawings

THIENO[2,3-C]IOSQUINOLINES FOR USE AS INHIBITORS OF PARP

The subject of the present invention is certain heterocyclic derivatives, including derivatives of thieno[2,3-c]isoquinolin-3-one and their use in therapy as inhibitors of poly(ADP-ribose) polymerase (PARP).

BACKGROUND OF INVENTION

Poly(ADP-ribose) polymerase or poly(ADP-ribose) synthase (PARS) is one of the enzymes (EC 2.4.2.30) which catalyse the transfer of ADP-ribose from NAD to the carboxyl groups of proteins. It is mainly found in the cell nucleus and for many years it has been considered that its activity is directed towards the maintenance of the integrity of the DNA sequence by in some way participating in the repair of damage undergone by the gene sequence after toxic or infective insults. Some histones, topoisomerase I and II, DNA ligase and other nuclear proteins are substrates of this enzyme. Moreover, PARP itself can undergo self-poly-ADP ribosylation.

The cDNA which codes for PARP has been cloned and the protein has been purified from tissues of many animal species, including man. The structure of PARP is available in various data banks, and consists of:
1. an amino terminal domain capable of binding DNA (42 kDa),
2. a central zone also called self-modification domain (which thus can be ADP-ribosylated and which on average weighs 16 kDa), and
3. a carboxy terminal domain which contains the catalytic site (55 kDa) and which has an amino acid composition and a tertiary structure highly conserved from drosophila to man.

The necessary and sufficient stimulus for activating the enzyme is damage to the DNA (formation of "nicks" or other lesions of the double helix) (de Murcia et al., 1992; Menisser-de Murcia et al., 1997). This commonly occurs by the action of strong oxidants and/or of highly reactive molecules such as the free radicals which form abundantly in the tissues in the course of various pathological situations. Nitric oxide can also directly or indirectly damage the DNA double helix, activate PARP and lead the cell to massive utilization of NAD and to ATP depletion (Szabò et al., 1996). Considering then that NAD is essential for oxidative phosphorylation and the resynthesis of ATP, it can be understood how cells which are in that situation are not capable of maintaining their ionic equilibria and can undergo degeneration both of necrotic and of apoptotic type. Excessive activation of PARP under the action of newly formed nitric oxide can occur in the central nervous system following activation of the glutamate receptors of the NMDA type associated with neuronal nitric oxide synthase (nNOS). It can also occur in other organs or tissues, since nitric oxide can be synthesized by the NOS of the endothelium or by the inducible NOS of the microglia and macrophages, and diffuse into the surrounding cells. Much experimental data seems to be in agreement with this hypothesis and it has been clearly demonstrated that by inhibiting PARP it is possible to reduce excitotoxic neuronal death or that due to free radicals in various types of neuronal culture (Schraufstatter et al., 1986; Cosi et al., 1994; Zhang et al., 1994). It has also been shown that baby mice with this enzyme knocked out are particularly resistant to cerebral tissue loss after occlusion of the medial cerebral artery or endocrine cell loss after administration of toxins. It has also been shown that cells taken from such mice are very resistant to oxidative stress (Eliasson et al., 1997; Endres et al., 1997; Pieper et al., 1999).

Thus the importance of having available pharmaceutically acceptable PARP inhibitors is clear.

DESCRIPTION OF INVENTION

The subject of the invention is compounds of formula I

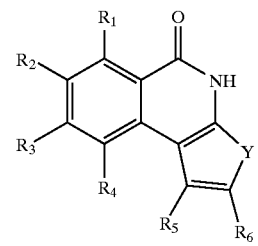

where Y is a hetero atom selected from sulphur (S), nitrogen (N) or oxygen (O),
$R_1$–$R_6$ are the same or different, and represent hydrogen, hydroxide, an $OR_7$ group, carboxy, $COOR_7$ group, amino group, $NHR_7$ group or halogen, or $R_5$ and $R_6$ taken together form a fused aromatic or non-aromatic 5- or 6-membered ring,
$R_7$ is a $C_1$–$C_6$ alkyl group, $C_2$–$C_6$ alkenyl group or $C_3$–$C_7$ cycloalkyl group possibly substituted with one or more hydroxy, $C_1$–$C_4$ alkoxy, carboxy, $C_1$–$C_4$ alkoxycarbonyl, amino, $C_1$–$C_6$ mono- or dialkylamino groups or halogen.
The invention further includes the non-toxic salts, solvates and physiologically equivalent derivatives of the compounds of formula I.

The compounds of formula I containing ionizable groups will in fact be able to form salts with pharmaceutically acceptable acids and bases such as hydrochloric, sulphuric, tartaric, maleic, citric, succinic, acetic, phosphoric, benzoic, methanesulphonic acid and the like or with bases such as alkali or alkaline earth metals, ammonium, alkylammonium and the like.

Examples of suitable solvates include the hydrated forms of the compounds I.

"Physiologically equivalent derivative" is understood to mean a compound capable of liberating a compound of formula I or an active metabolite thereof in vivo.

Examples of $C_1$–$C_6$ alkyl groups include methyl, ethyl, isopropyl, n-propyl and butyl.

Examples of $C_2$–$C_6$ alkenyl groups include vinyl and allyl.

Examples of $C_3$–$C_7$ cycloalkyl groups include cyclopropyl, cyclopentyl and cyclohexyl.

Examples of $C_1$–$C_4$ alkoxy groups include methoxy and ethoxy.

Examples of $C_1$–$C_4$ alkoxycarbonyl groups include methoxycarbonyl and ethoxycarbonyl.

Examples of $C_1$–$C_6$ alkylamino groups include methylamino, dimethylamino, methylethylamino and isopropylamino.

The term halogen refers to chlorine, bromine, iodine or fluorine, preferably chlorine or fluorine.

Preferably, in compounds of formula I, Y is an atom of sulphur.

Compounds more particularly preferred are those wherein $R_1$–$R_6$ are hydrogen or one of $R_1$–$R_6$ is different from hydrogen, such as ioniz, alkoxy, carboxy, alkoxycarbonyl, amino, alkylamino or halogen as defined above and the others are hydrogen.

In a particularly preferred group of compounds, $R_4$ is hydrogen or a group different from hydrogen, preferably ioniz or alkoxy or amino, Y is nitrogen, oxygen or sulphur, preferably sulphur, and $R_1$, $R_2$, $R_3$, $R_5$ and $R_6$ are hydrogen.

The invention also provides a method for the preparation of the compounds of formula I, which comprises the reaction of a compound of formula

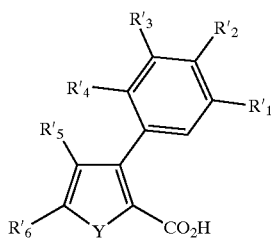

(II)

wherein $R'_1$–$R'_6$ are $R_1$–$R_6$ as defined above or are groups convertible into $R_1$–$R_6$, with thionyl chloride followed by reaction with sodium azide and subsequent Curtius rearrangement (J. Heterocyclic Chem., 1978, 15, 301–305) by thermolysis.

An example of a convertible group is nitro, which can be reduced to amino.

The compounds II are known or can be obtained by known methods. In the case of the compounds wherein Y is sulphur, for example, the compounds of formula II can be obtained in accordance with the following scheme:

SCHEME 1

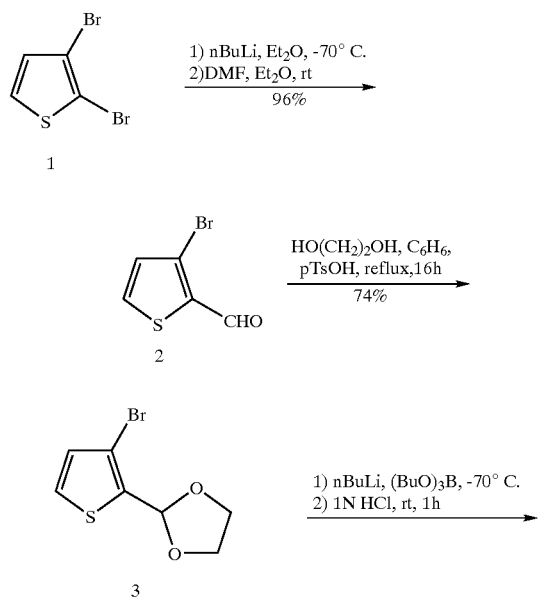

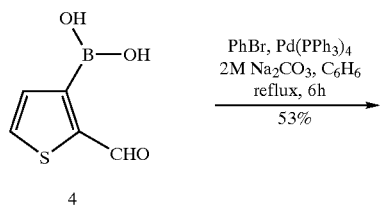

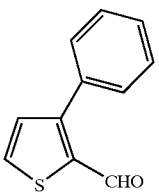

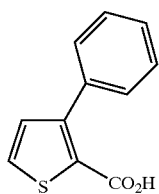

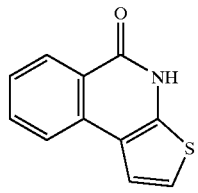

3-bromothiophen-2-aldehyde (2) was obtained from commercially available 2,3-dibromothiophen (1) via 3-bromothienyllithium and reaction with N,N-dimethylformamide. The aldehyde 2 was protected by reaction with ethylene glycol to give 2-(3-bromo-2-thienyl)-1,3-dioxolane (3). The latter derivative was converted into 2-formyl-3-thiopheneboronic acid (4) using halogen-metal interconversion between the substrate (3) and butyllithium at –70° C., followed by treatment with tributyl borate and subsequent hydrolysis. The thienylboronic derivative 4 is a very useful intermediate, in fact it can be condensed with various bromo-aromatic compounds. Thus, palladium-catalysed condensation reaction of the derivative 4 with bromobenzene in aqueous sodium carbonate-ethanol mixture as solvent gave 3-phenyl-thiophen-2-carboxaldehyde (5). Oxidation of 5 with Jones' reagent yielded 3-phenyl-thiophen-2-carboxylic acid (6). Chlorination of 6 with thionyl chloride followed by reaction with sodium azide yielded the acyl azide intermediate which on thermolysis in boiling o-dichlorobenzene gave the derivative thieno[2,3-c]isoquinolin-5(4H)-one (7).

In the case of the synthesis of compounds in which $R_4$ are amino groups or in the case where suitable bromo-aromatic intermediates are not available, the following alternative route can be utilized:

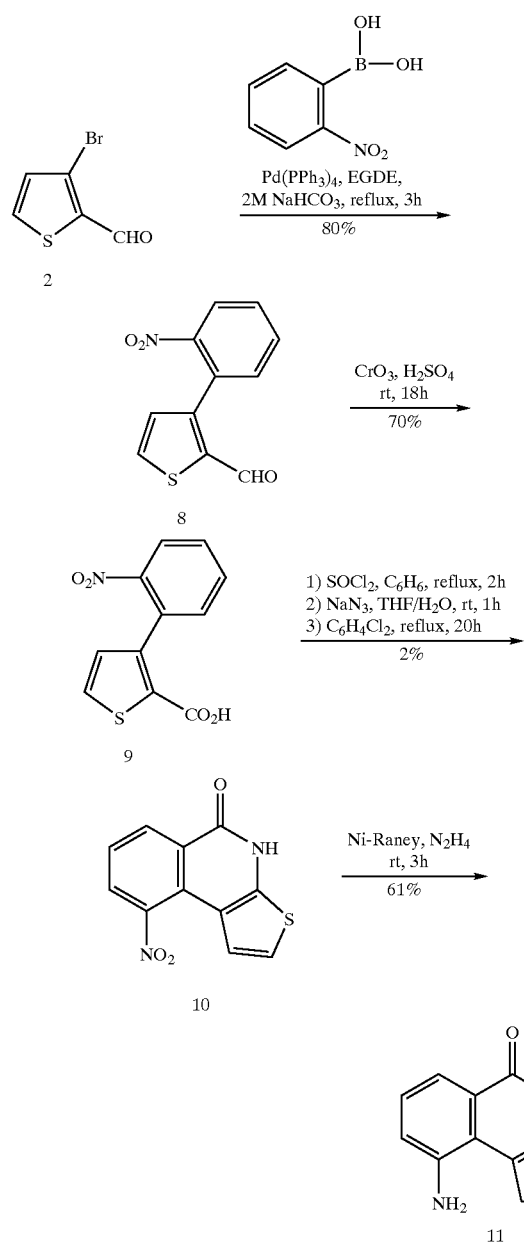

SCHEME 2

The intermediate 3-bromothiophen-2-aldehyde (2) can be condensed with various commercially available or synthetic 2-substituted phenylboronic acids, in particular with 2-nitrophenylboronic acid to obtain 3-(2-nitrophenyl)-thiophen-2-aldehyde (8). Oxidation of 8 with Jones' reagent yielded 3-(2-nitrophenyl)-thiophen-2-carboxylic acid (9). Chlorination of 9 with thionyl chloride followed by reaction with sodium azide yielded the acyl azide intermediate which on thermolysis in refluxing o-dichlorobenzene gave the intermediate 9-nitrothieno[2,3-c]isoquinolin-5(4H)-one (10) which on reduction with hydrazine and Raney nickel as catalyst gave the derivative 9-aminothieno[2,3-c]isoquinolin-5(4H)-one (11).

In the case of compounds in which Y is nitrogen, for example, the compounds of formula II can be obtained by following schemes 1 and 2 analogously replacing the compound 3-bromo-thiophen-2-aldehyde (2) with the intermediate 3-iodopyrrol-2-aldehyde obtainable by the following scheme (Bull. Soc. Chim. 1973, 1, 351–359):

SCHEME 3

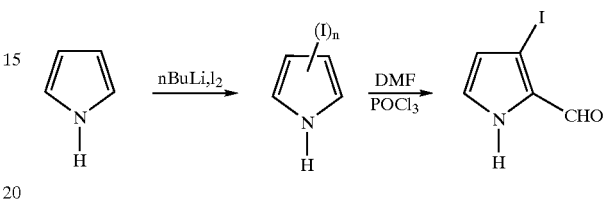

In the case of compounds in which Y is oxygen, the compounds of formula II can be obtained in a manner similar to that reported in the literature for furo[2,3-c]isoquinolinone derivatives (J. Heterocyclic Chem., 1978, 15, 301–305).

The compounds of formula I can be used both for the prevention and for the treatment of vast sectors of human and animal pathology. In particular, they can be utilized in the prevention and treatment of:

1) Tissue Damage due to Ischaemia and Reperfusion. Such damage, with consequent apoptopic or necrotic cell death, can give rise to various neurological diseases such as: stroke, cerebral or spinal trauma, epileptic events, cerebral damage due to cardiac arrest and/or to situations of prolonged hypotension, respiratory arrest, carbon monoxide or cyanide poisoning, drowning or hydrocephalus. The cerebral insult can also be of a toxic nature (excitotoxins and other chemical products), iatrogenic (including surgical) and due to ionizing radiation. Tissue damage due to ischaemia and reperfusion can also affect the myocardium and be present in many cardiopathies such as post-infarction, during and after coronary by-pass surgery, on the resumption of perfusion in transplanted hearts and indeed any time when for surgical reasons cardiac arrest is performed, and blood reperfusion is initiated. The kidney, the liver, the intestine and skeletal musculature are susceptible to damage due to ischaemia and reperfusion. This occurs in septic, endotoxic, haemorrhagic and compression shock. It also occurs in strangulated hernia, strangulation of intestinal loops, and after prolonged compression of joints in multiply traumatised patients.

2) Degenerative Diseases. The inhibition of PARP can extend the reproductive capacity of various cells and hence be utilized to prevent diseases typically associated with aging. Particularly to be mentioned are degenerative diseases of the central nervous system such as Parkinson's disease, Alzheimer's dementia, Huntington's chorea, amyotrophic lateral sclerosis, macular degeneration and retinal ischaemia. Other degenerative diseases include the aging of the skin, degenerative diseases of the muscles (muscular dystrophy), bones (osteoporosis) and vascular system (atherosclerosis), diabetes and diseases of the immune system present during senescence.

3) Inflammatory Diseases. Excessive activation of PARP can be harmful in various diseases of predominantly inflammatory nature, both of the central nervous system and of peripheral organs. The compounds of the invention are thus useful in the following pathological situations: multiple sclerosis and other demyelinizing diseases, Guillain-Barré syndrome, neuralgias of the trigeminus and/or other cranial nerves, peripheral neuropathies and other chronic pain, osteoarthritis, inflammatory diseases of the intestine (Crohn's disease, ulcerative colitis, and other forms of colitis).

4) Tumour Diseases. PARP inhibitors can facilitate the death of tumour cells induced by ionizing agents or by chemotherapeutic agents and will be used, both alone and in combination with other treatments, in the prevention and in the therapy of various forms of cancer, leukaemia and/or sarcoma, whether these are primary or associated with AIDS.

For the intended pharmaceutical uses, the compounds of formula I can be administered alone or in the form of a conventional pharmaceutical preparation, the form of which obviously depends on the choice of the administration route. For example, for oral administration, they can be formulated in the form of tablets, capsules, granules, powders, syrups or the like, or, for parenteral administration, they can be formulated in the form of injections, suppositories or the like. These pharmaceutical preparations can be produced by conventional methods using ingredients generally known in the technology, such as excipients, binders, disintegration agents, lubricants, stabilizers, modifiers and the like. Although the dosage can vary depending on the symptoms and the age of the patient, the nature and severity of the disease or disorder and on the route and mode of administration, in the case of oral administration to an adult human patient, the compounds of the present invention can commonly be administered at a total daily dosage lying between 1 and 1000 mg, preferably between 5 and 500 mg, either in a single dose or in subdivided doses, for example from one to three times a day; in the case of an intravenous injection, a dosage lying between 0.1 and 100 mg, preferably lying between 0.5 and 50 mg, can be administered from one to three times a day.

The following Examples illustrate the invention in more detail.

EXAMPLE 1

Thieno[2,3-c]isoquinolin-5(4H)-one a. 3-Bromothiophen-2-aldehyde (2)

A 1.4 N solution of n-butyllithium in hexane (34 ml) was added dropwise to 2,3-dibromo-thiophen (1) (10 g, 41.1 mmol) in anhydrous ether (20 ml) at −70° C. After 10 mins, the solution was transferred into a solution of N,N-dimethylformamide (4.8 ml) in anhydrous ether (15 ml) and the reaction mixture was left for 30 mins with stirring. The reaction was stopped by addition of a 10% solution of hydrochloric acid (20 ml). The ether layer was washed with a solution of bicarbonate, dried ($Na_2SO_4$), and evaporated under reduced pressure to give the crude aldehyde compound 2 (7.54 g, 39.5 mmol, 96% yield) as an oil.

$^1$H-NMR ($CDCl_3$) ä 7.19 (d J=5.1 Hz, 1H, th-H), 7.45 (d J=5.2, 1H, th-H), 10.02 (s, 1H, CHO).

b. 2-(3-Bromo-2-thienyl)-1,3-dioxolane (3)

3-Bromothiophen-2-aldehyde (2) (7.44 g, 39 mmol), ethylene glycol (2.7 ml, 48 mmol), anhydrous benzene (130 ml) and a few crystals of p-toluenesulphonic acid were refluxed in a Dean-Stark apparatus until no more water separated. The benzene layer was washed with a solution of bicarbonate, dried ($Na_2SO_4$), and evaporated under reduced pressure to give the derivative 3 (6.8 g, 28.9 mmol, 74% yield) as an oil.

$^1$H-NMR ($CDCl_3$) ä 3.80–4.06 (m, 4H, diox), 6.03 (s, 1H, diox), 6.85 (d J=5.2 Hz, 1H, th-H), 7.16 (d J=5.7 Hz, 1H, th-H).

c. 2-Formylthiophen-3-boronic Acid (4)

A 1.1 N solution of n-butyllithium in hexane (28 ml). was added dropwise (10 mins) to a solution of 2-(3-bromo-2-thienyl)-1,3-dioxalane (3) (6.6 g, 28.1 mmol) in anhydrous ether (30 ml) at −70° C. After stirring for 10 mins, butyl borate (9.1 ml, 33.7 mmol) in anhydrous ether (20 ml) was added in a single portion. The reaction mixture was stirred for 4 hrs at −70° C. and then left to return to room temperature. 1 N hydrochloric acid (20 ml) was added, and the mixture was left for 1 hr with stirring. The aqueous phase was extracted with ether and the combined ether phases were washed with a solution of sodium bicarbonate, dried ($Na_2SO_4$), and evaporated under reduced pressure to give the intermediate (4) (2.2 g, 14.1 mmol, 50% yield) as a brown solid.

$^1$H-NMR ($CDCl_3$) ä 7.0 (brs, 2H, OH), 7.77 (d J=5.1 Hz, 1H, th-H), 7.85 (d J=5.2, 1H, th-H), 9.75 (s, 1H, CHO).

d. 3-Phenylthiophen-2-aldehyde (5)

2-Formylthiophen-3-boronic acid (4) (0.89 g, 5.7 mmol) dissolved in 96% ethanol (15 ml) was added dropwise to a mixture of 2-bromobenzene (0.66 ml, 6.2 mmol) in benzene (12 ml), ($Ph_3P)_4Pd$ (197 mg, 0.15 mmol) and an aqueous solution of 2M $Na_2CO_3$ (6.3 ml). The reaction mixture was then refluxed for 6 hrs. Then the mixture was cooled to room temperature, the solvent was partially removed under reduced pressure and the resulting mixture was extracted with ethyl ether (4×100 ml). The combined organic layer was washed with a saturated solution of NaCl, dried ($Na_2SO_4$), and evaporated under reduced pressure. The mixture was chromatographed using 95/5 petroleum ether/ethyl acetate, thus giving the derivative (5) (0.575 g, [lacuna] mmol, 53% yield).

$^1$H-NMR ($CDCl_3$) ä 7.19 (d J=5.0 Hz, 1H, th-H), 7.40–7.43 (m, 5H, Ph-H), 7.70 (d J=5.2, 1H, th-H), 9.83 (s, 1H, CHO).

e. 3-Phenylthiophen-2-carboxylic Acid (6)

8N Jones' reagent (ca. 10 ml) was added dropwise to a solution of 3-phenylthiophen-2-aldehyde (5) (0.58 g, 3.1 mmol) in 32 ml of acetone, until an orange colour persisted. The mixture was stirred at room temperature for 18 hrs. Isopropanol (5 ml) was added to remove the excess Jones' reagent and the mixture was then filtered, the organic solvents were evaporated under vacuum and extracted with ethyl acetate (4×100 ml). The combined organic layer was washed with a saturated solution of NaCl, dried ($Na_2SO_4$), and evaporated under reduced pressure. The mixture was then chromatographed using 95/5 chloroform/methanol, thus giving the compound (6) (0.44 g, 1.36 mmol, 46% yield) (M. Pt. 200–202° C.). $^1$H-NMR ($CDCl_3$) ä 6.87–7.37 (m, 5H, Ph-H) 7.05 (d J=5.0 Hz, 1H, th-H4), 7.53 (d J=5.0 Hz, 1H, th-H5).

f. Thieno[2,3-c]isoquinolin-5(4H)-one (7)

0.08 ml of thionyl chloride were added to a solution of 3-phenylthiophen-2-carboxylic acid (6) (0.138 g, 0.68 mmol) in 2 ml of anhydrous benzene and the mixture was refluxed for 2 hrs. The solvent and the excess thionyl chloride were removed under vacuum and the residue was taken up using 3 ml of THF, and $NaN_3$ (0.066 g, 1.02 mmol) in 1 ml of water was added rapidly to this stirred solution at 0° C. The mixture was left for 1 hr at room temperature with stirring, poured into 10 ml of crushed ice and water and extracted with ethyl ether (4×10 ml) and the separated organic layer was washed, dried and evaporated under vacuum. The residue was dissolved in 1 ml of o-dichlorobenzene and then added dropwise to 3 ml of boiling o-dichlorobenzene with stirring. The mixture was refluxed for 5 hrs, then cooled and evaporated. The mixture was subjected to flash chromatography, elution with 90:10 petroleum ether-ethyl acetate giving the end compound (7) (0.061 g, 0.3 mmol, 44% yield) as a pure solid (M. Pt. 266–268° C.); IR: 2849, 1647 cm$^{-1}$ (NHCO).

$^1$H-NMR (DMSO) ä 7.23 (d J=5.6 Hz, 1H, th-H1), 7.51 (m, 1H, th-H), 7.70 (d J=5.3 Hz, 1H, th-H1), 7.78 (m, 1H, Ph-H), 8.10 (dd J=7.4, 1.1 Hz, 1H, Ph-H), 8.25 (dd, J=8.0, 0.9 Hz, 1H, Ph-H), 12.3 (s, 1H, NH). $^{13}$C-NMR (CDCl$_3$) ä 116.4, 119.2, 120.6, 122.6, 123.3, 126.2, 128.4, 133.1, 134.1, 139.9, 163.2.

The following compounds were prepared by condensation of the derivative (4) with 2-methoxybromobenzene, according to the procedure of Example 1.

EXAMPLE 2 g. 9-Hydroxythieno[2,3-c]isoquinolin-5(4H)-one (M. Pt.: 298–301° C.) $^1$H-NMR (CDCl$_3$) ä 7.01 (d, J=5.7 Hz, 1H, th-H1), 7.15 (dd, J=7.83 Hz, J=1.1 Hz, 1H, Ph-H6), 7.28 (t, J=7.9 Hz, 1H, Ph-H7), 7.82 (dd J=7.8 Hz, J=1.1 Hz, 1H, Ph-H8), 8.05 (d J=5.7 Hz, 1H, th-H2).

EXAMPLE 3 h. 9-Methoxythieno[2,3-c]isoquinolin-5(4H)-one (M. Pt.: 198–200° C.) $^1$H-NMR (CDCl$_3$) ä 4.00 (s, 3H, OCH$_3$), 6.95 (d J=5.7 Hz, 1H, th-H1), 7.20 (m, 1H, Ph-H6), 7.44 (t, J=8.0 Hz, 1H, Ph-H7), 7.98 (d J=5.7, Hz, 1H, th-H2), 8.13 (dd J=8.0, 1.1 Hz, 1H, Ph-H8).

The compound of Example 2 is obtained from the compound of Example 3 by reaction with boron tribromide.

EXAMPLE 4 i. 3-(2-Nitrophenyl)-thiophen-2-aldehyde (8)

The compound 3-bromothiophen-2-aldehyde (2) (5.20 g, 27 mmol), solubilized in ethylene glycol dimethyl ether (105 ml) was treated with (Ph$_3$P)$_4$Pd (936 mg, 0.81 mmol), with 2-nitrophenylboronic acid (5 g, 30 mmol) and an aqueous solution of 2M NaHCO$_3$ (70 ml). The reaction mixture was then refluxed for 5 hrs. Then the mixture was cooled to room temperature, the solvent was partially removed under reduced pressure and the resulting mixture was extracted with ethyl acetate (4×100 ml). The combined organic layer was washed with a saturated solution of NaCl, dried (Na$_2$SO$_4$), and evaporated under reduced pressure. The mixture was chromatographed using 80/20 petroleum ether/ethyl acetate, thus giving the derivative (8) (4.5 g, 83% yield).

$^1$H-NMR (CDCl$_3$) ä 7.04 (d J=5.1 Hz, 1H, th-H), 7.45 (dd J=5.2, 0.9 Hz, 1H, th-H), 7.58–7.74 (m, 3H, Ph-H), 7.98 (dd J=8.0, 0.9 Hz, 1H, Ph-H), 9.61 (s, 1H, CHO).

l. 3-Phenylthiophen-2-carboxylic Acid (9) [sic]

8N Jones' reagent (ca. 30 ml) was added dropwise to a solution of 3-(2-nitrophenyl)-thiophen-2-aldehyde (8) (4.4 g, 3.1 mmol) in 32 ml of acetone, until an orange colour persisted. The mixture was left at room temperature for 18 hrs with stirring. Isopropanol (20 ml) was added to remove the excess Jones' reagent and the mixture was then filtered, the organic solvents were removed under vacuum and extracted with ethyl acetate (4×100 ml). The combined organic layer was washed with a saturated solution of NaCl, dried (Na$_2$SO$_4$), and evaporated under reduced pressure. The mixture was then chromatographed using 95/5 chloroform/methanol, thus giving the compound (9) (3.6 g, 66% yield).

$^1$H-NMR (CDCl$_3$) ä 6.80 (d J=5.1 Hz, 1H, th-H), 7.25 (dd J=5.2, 0.9 Hz, 1H, th-H), 7.30–7.60 (m, 3H, Ph-H), 7.95 (dd J=8.0, 0.9 Hz, 1H, Ph-H).

m. 9-Nitrothieno[2,3-c]isoquinolin-5(4H)-one (10)

2 ml of thionyl chloride were added to a solution of 3-(2-nitrophenyl)thiophen-2-carboxylic acid (9) (3.5 g, 14 mmol) in 20 ml of anhydrous benzene and the mixture was refluxed for 2 hrs. The solvent and the excess thionyl chloride were removed under vacuum and the residue was taken up using 50 ml of THF, and NaN$_3$ (1.37 g, 21 mmol) in 10 ml of water was added rapidly to this stirred solution at 0° C. The mixture was left for 1 hr at room temperature with stirring, poured into 100 ml of ice and water and extracted with ethyl ether (4×50 ml), the separated organic layer was dried over anhydrous sodium sulphate and leaving it for 2 hrs with stirring. It was evaporated under vacuum and coevaporated with anhydrous benzene (3×50 ml). It is evaporated and the residue was solubilized in 60 ml of o-dichlorobenzene and refluxed using a Dean-Stark apparatus. The mixture was left under reflux for 20 hrs with stirring, then cooled and evaporated. The mixture was subjected to flash chromatography, and elution with chloroform yielded the compound 9-nitrothieno-[2,3-c]-isoquinolin-5 (4H)-one (0.075 g, 2.2% yield) as a yellow solid (M. Pt, 255–258° C.).

$^1$H-NMR (DMSO) ä 6.83 (d J=5.8 Hz, 1H, Th-H), 7.22 (d J=5.8 Hz, 1H, Th-H), 7.61 (t J=7.9 Hz, 1H, Ph-H), 8.16 (dd J=7.8, 0.8 Hz, 1H, Ph-H), 8.47 (dd, J=8.0, 0.8 Hz, 1H, Ph-H), 12.8 (bs, 1H, NH).

n. 9-Aminothieno[2,3-c]isoquinolin-5(4H)-one (11)

The compound 9-nitrothieno[2,3-c]isoquinolin-5(4H)-one (0.028 g, 0.113 mmol) was solubilized in dimethoxyethanol (20 ml), Raney nickel (ca. 10 mg) was added, and the mixture treated dropwise with hydrazine hydrate (ca. 1 ml). The mixture was left for 3 hrs with stirring, filtrated on Celite and evaporated under vacuum. The residue was chromatographed eluting with 99/1 chloroform/methanol to give 9-aminothieno[2,3-c]isoquinolin-5(4H)-one (10) [sic] as the pure solid (0.015 g, 61% yield) (M. Pt. 297–299° C.).

$^1$H-NMR (DMSO) ä 5.31 (s, 2H, NH$_2$), 7.11 (m, 2H, Ph-H and Th-H), 7.17 (t J=7.8 Hz, 1H, Ph-H), 7.57 (dd J=7.8, 1.3 Hz; 1H, Ph-H), 7.83 (d, J=5.8 Hz, 1H, Th-H), 12.21 (bs, 1H, NH).

Pharmacological Activity

The inhibitory activity of the compounds of Examples 1–3 on the enzyme poly(ADP-ribose) polymerase (PARP) was evaluated in hippocampus section culture models of organotypical cerebral ischaemia, as was their activity in models of cerebral ischaemia in vitro (primary neuronal cultures) and in vivo (occlusion of the medial cerebral artery (MCAO) in rats).

The methods used were:

1) Purification and Measurement of Activity Against PARP

The activity on PARP was evaluated using purified PARP derived from foetal calf thymus, as per Ito et al. (J. Biol. Chem. 274: 3647, 1979). A portion (ca. 1 g) of thymus was homogenized in 4 volumes of a buffer containing 50 mM Tris-HCl, 0.3M NaCl, 10% glycerol, 10 mM mercaptoethanol and 50 mM sodium bisulphite. After centrifugation (12,000 rpm/15 mins), the supernatant was treated with 150 ml of 3.75% protamine sulphate and stirred in ice for 5 minutes. The enzymatic activity was further purified by affinity chromatography on a DNA-agarose column (25×0.5 cm; 0.75 mg DNA/ml of 4% agarose bed). The active fractions were used for the activity tests carried out as per Banasik et al. (J. Biol. Chem. 267: 1569, 1992). The test mixture (100 ml) containing 100 mM Tris-HCl pH 8, 50 mg of sonicated DNA, 60 ml of partially purified enzyme preparation and 0.2 mC of 3[H]NAD (1–5 Ci/mmol, New England Nuclear, Boston, Mass., USA) was incubated at 37° C. for 30 mins. The reaction was terminated with 10% of trichloroacetic acid and the radioactivity associated with the protein was evaluated in a liquid scintillation spectrometer.

2) The biological activity was evaluated in primary neuronal cultures exposed to oxygen and glucose deprivation (see: Neuropharmacology 38: 1007–1619) and in vivo in rats with MCA [sic]. The volume of the infarct was measured 72 hrs after the occlusion using a method described previously (Cozzi et al., J. Cerebrali Blood Flow Metabolism 19: 771–777; 1999).

TABLE $IC_{50}$ ($\mu$M) of PARP inhibitors tested on enzyme prepared from bovine thymus

| Compound | $IC_{50}$ ($\mu$M) |
|---|---|
| Benzamide | 90 |
| Phenanthridinone | 12 |
| DPQ (UPF 707) | 10 |
| Example 1 | 0.3 |
| Example 2 | 0.1 |
| Example 3 | 0.3 |
| Example 4 | 0.05 |

Conclusion:

The compounds of the invention are potent PARP inhibitors.

3) Biological Activity of PARP Inhibitors in Ischaemia Models

Some PARP inhibitors were tested on neuronal death induced by ischaemia in primary neuronal cultures exposed to a period of oxygen and glucose deprivation (see: Neuropharmacology 38: 1007–1619) and the results showed that the PARP inhibitors exert a potent inhibitory activity on post-ischaemic neuronal death of the necrotic type.

Among the compounds of the invention, the compound of Example 1 was found to be extremely potent in reducing post-ischaemic neuronal death, having a ca. 3 micromolar $IC_{50}$.

The neuroprotective activity of the compound of Example 1 was also tested in the MCAO model in rats. In this stroke model, the compound (3–10 mg/kg i.p.) reduced by 40% the volume of necrotic brain induced by the permanent occlusion of the medial cerebral artery.

What is claimed is:

1. A compound of formula I,

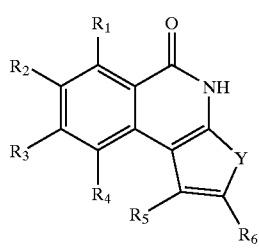

wherein

Y is a hetero atom selected from sulphur (S), or nitrogen (N), $R_1$, $R_2$, $R_3$, $R_4$, $R_5$ and $R_6$ are the same or different, and each represent hydrogen, hydroxy, $OR_7$, carboxy, $COOR_7$, amino, $NHR_7$ or halogen, or $R_5$ and $R_6$ taken together form a fused non-aromatic 5- or 6-membered ring, $R_7$ is $C_1$–$C_6$ alkyl, $C_2$–$C_6$ alkenyl or $C_3$–$C_7$ cycloalkyl optionally substituted with one or more group selected from hydroxy, $C_1$–$C_4$ alkoxy, carboxy, $C_1$–$C_6$ alkoxycarbonyl, amino, $C_1$–$C_6$ mono- or di-alkylamino or halogen;

or a salt, solvate, or physiologically equivalent derivative thereof.

2. A compound according to claim 1, wherein Y is sulphur.

3. A compound according to claim 1, wherein $R_1$, $R_2$, $R_3$, $R_4$, $R_5$ and $R_6$ are each hydrogen.

4. A compound according to claim 1, wherein $R_4$ is hydrogen, hydroxy or alkoxy or amino, and $R_1$, $R_2$, $R_3$, $R_5$ and $R_6$ are each hydrogen.

5. A compound according to claim 4, wherein Y is sulphur.

6. A compound according to claim 1 selected from:
thieno[2,3-c]isoquinolin-5(4H)-one,
9-hydroxythieno[2,3-c]isoquin-5(4H)-one,
9-methoxythieno[2,3-c]isoquin-5(4H)-one,
or a salt, solvate, or physiologically equivalent derivative thereof.

7. A pharmaceutical composition comprising a compound of claim 1, mixed with a suitable vehicle.

8. A method for prophylaxis or treatment of damage due to ischemia and reperfusion, degenerative diseases, inflammatory diseases, tumour diseases, leukaemia and/or sarcoma, which comprises administration of an effective quantity of a compound of claim 1.

9. A compound according to claim 1, wherein one of $R_1$, $R_2$, $R_3$, $R_4$, $R_5$ and $R_6$ is hydroxy, alkoxy, alkoxycarbonyl, amino, alkylamino or halogen, and the others are hydrogen.

10. A method for inhibiting poly(ADP-ribose) polymerase in an animal or a human, which comprises the administration of an effective quantity of a compound of claim 1 to said animal or said human.

11. A compound of formula I,

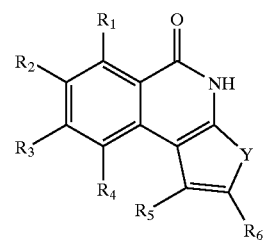

wherein

Y is oxygen, $R_1$, $R_2$, $R_3$, $R_4$, $R_5$ and $R_6$ are the same or different, and each represent hydrogen, hydroxy, $OR_7$, carboxy, $COOR_7$, amino, $NHR_7$ or halogen, or $R_5$ and $R_6$ taken together form a fused aromatic or non-aromatic 5- or 6-membered ring;

$R_7$ is $C_2$–$C_6$ alkenyl or $C_3$–$C_7$ cycloalkyl optionally substituted with one or more group selected from hydroxy, $C_1$–$C_4$ alkoxy, carboxy, $C_1$–$C_6$ alkoxycarbonyl, amino, $C_1$–$C_6$ mono- or di-alkylamino or halogen;

or a salt, solvate, or physiologically equivalent derivative thereof.

12. A compound according to claim 11, wherein $R_1$, $R_2$, $R_3$, $R_4$, $R_5$ and $R_6$ are each hydrogen.

13. A compound according to claim 11, wherein $R_4$ is hydrogen, hydroxyl or amino or $OR_7$, and $R_1$, $R_2$, $R_3$, $R_5$ and $R_6$ are each hydrogen.

14. A pharmaceutical composition comprising a compound of claim 11, mixed with a suitable vehicle.

15. A method for prophylaxis or treatment of damage due to ischemia and reperfusion, degenerative diseases, inflammatory diseases, tumour diseases, leukaemia and/or sarcoma, which comprises administration of an effective quantity of a compound of claim 11.

16. A compound according to claim 11, wherein one of $R_1$, $R_2$, $R_3$, $R_4$, $R_5$ and $R_6$ is hydroxy, $OR_7$, alkoxycarbonyl, amino, alkylamino or halogen, and the others are hydrogen.

17. A method for inhibiting poly(ADP-ribose) polymerase in an animal or a human, which comprises the administration of an effective quantity of a compound of claim 11 to said animal or said human.

\* \* \* \* \*

UNITED STATES PATENT AND TRADEMARK OFFICE
CERTIFICATE OF CORRECTION

PATENT NO. : 6,989,388 B2
APPLICATION NO. : 10/415601
DATED : January 24, 2006
INVENTOR(S) : Roberto Pellicciari and Flavio Moroni It is certified that error appears in the above-identified patent and that said Letters Patent is hereby corrected as shown below:

On the Cover page (54), please delete the word "losoquinolines" in the title and insert therefor
--Isoquinolines--.

On the Cover page (73), please delete the City of Residence of Flavio Moroni which is listed as "Florence (IT)" and insert therefor --Firenze (IT)--.

Signed and Sealed this

Eleventh Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,388 B2
APPLICATION NO. : 10/415601
DATED : January 24, 2006
INVENTOR(S) : Roberto Pellicciari and Flavio Moroni It is certified that error appears in the above-identified patent and that said Letters Patent is hereby corrected as shown below:

Column 12, lines 11, 23, 64, for claim language reading "or a salt, solvate, or physiologically equivalent derivative" each occurrence should read --or a salt or a solvate --.

Column 12, line 27, cancel text beginning with "prophylaxis or treatment" to and ending "and/or sarcoma", Column 12, line 30, and insert -- treatment of stroke, arthritis, colitis, diabetes and/or parkinson's disease in an animal or human --.

Column 12, line 31, after text "claim 1", insert -- to sad animal or said human -- .

Column 13, line 6, cancel text beginning "prophylaxis or treatment" to and ending "and/or sarcoma", Column 13, line 9, and insert -- treatment of stroke, arthritis, colitis, diabetes and/or parkinson's disease in an animal or human --.

Column 13, line 10, after text "claim 11", insert -- to said animal or said human --.

Signed and Sealed this

First Day of May, 2007

JON W. DUDAS
*Director of the United States Patent and Trademark Office*